United States Patent [19]

Lindley et al.

[11] Patent Number: 4,894,482

[45] Date of Patent: Jan. 16, 1990

[54] PROCESS FOR DRYING HYDROGEN FLUORIDE-CARBOXYLIC ACID MIXTURES

[75] Inventors: Daniel D. Lindley, Eppstein, Fed. Rep. of Germany; Carl D. Murphy, Corpus Christi, Tex.

[73] Assignee: Hoechst Celanese Corporation, Sommerville, N.J.

[21] Appl. No.: 281,302

[22] Filed: Dec. 6, 1988

[51] Int. Cl.$^4$ .............................................. C09C 45/46
[52] U.S. Cl. ...................................... 568/319; 568/42; 568/43; 568/63; 568/64; 562/490; 562/494; 562/606; 562/608; 562/609
[58] Field of Search ...................... 568/319, 42, 43, 63, 568/64; 562/490, 494, 606, 608, 609

[56] References Cited

U.S. PATENT DOCUMENTS

| | | | |
|---|---|---|---|
| 2,388,156 | 10/1945 | Kelley | 260/683.4 |
| 4,524,217 | 6/1985 | Davenport et al. | 564/223 |
| 4,568,763 | 2/1986 | Davenport et al. | 560/142 |
| 4,593,125 | 6/1986 | Davenport et al. | 568/319 |
| 4,607,125 | 8/1986 | Mott | 568/319 |
| 4,663,485 | 5/1987 | Murphy et al. | 568/319 |
| 4,692,546 | 9/1987 | Davenport | 560/130 |

FOREIGN PATENT DOCUMENTS 0071293 2/1983 European Pat. Off. .

OTHER PUBLICATIONS

Dann et al., Annalen der Chemie 587 Band, pp. 1 to 15 (1954) (English translation provided).
Simons et al., Journal of the American Chemical Society 61, 1795, and 1796 (1939).

*Primary Examiner*—Bruce Gray
*Attorney, Agent, or Firm*—Donald R. Cassady; Marvin Turken

[57] ABSTRACT

A process is provided for removing water from a mixture of hydrogen fluoride (HF), a carboxylic acid, e.g., acetic acid, and water by extractive distillation in the presence of a Lewis base as solvent, which does not azeotrope with water, forms bonds with the HF and carboxylic acid which can be broken by heat and has a boiling point at atmospheric pressure at least about 20° C. above that of the carboxylic acid, e.g., N-methyl-2-pyrrolidone, and taking off an overhead vapor comprising a major proportion of the water in said mixture. The extractive distillation may be advantageously integrated in an overall process with the production of an aromatic ketone, e.g., 4-hydroxyacetophone, by the Friedel-Crafts acylation of an aromatic compound, e.g., phenol, with the carboxylic acid, using HF as catalyst, to produce a product mixture comprising the aromatic ketone, HF, carboxylic acid and water, and the removal of aromatic ketone from the product mixture by means of a solvent assisted distillation.

17 Claims, 1 Drawing Sheet

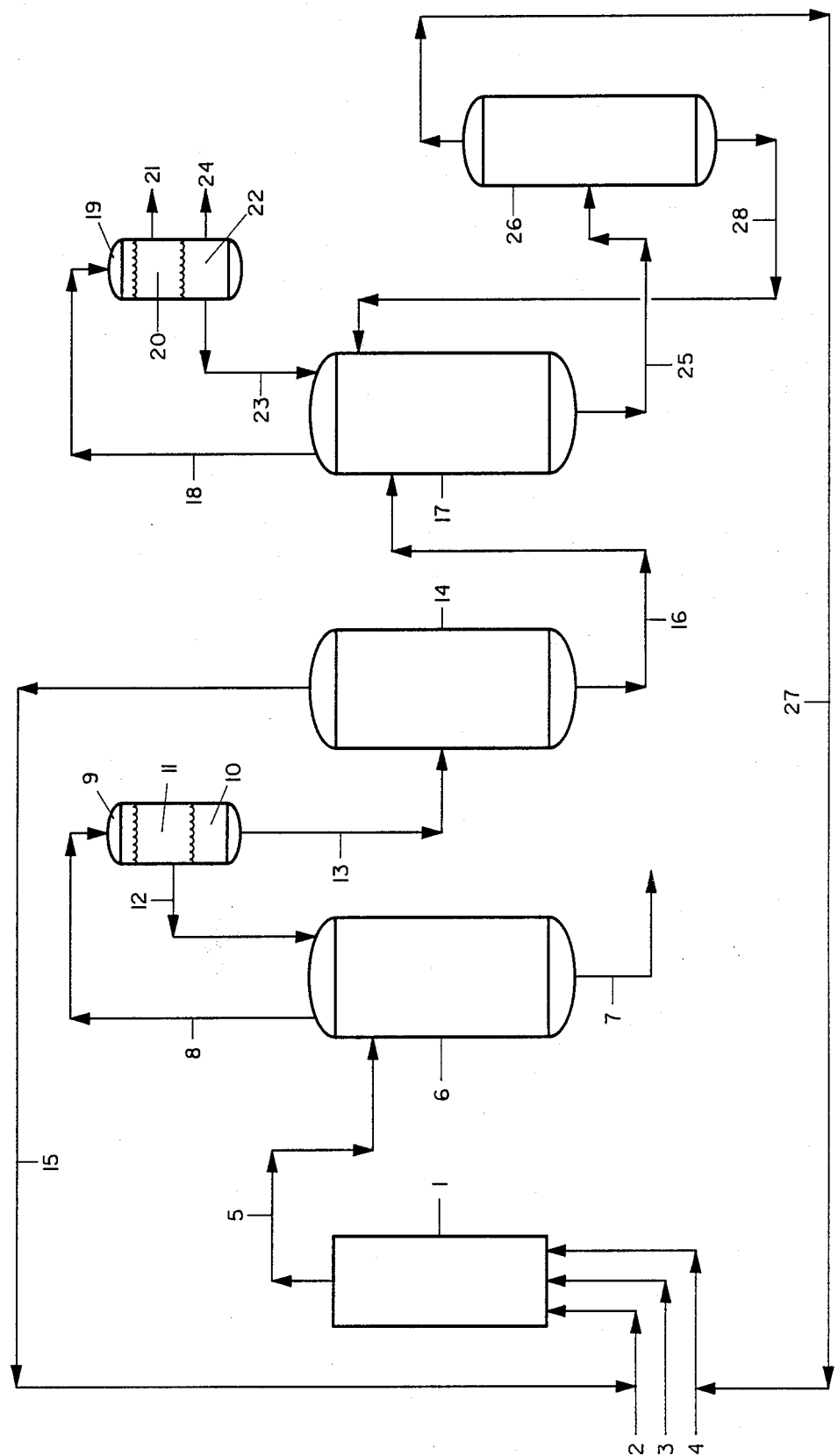

PROCESS FOR DRYING HYDROGEN FLUORIDE-CARBOXYLIC ACID MIXTURES

BACKGROUND OF THE INVENTION

1. Field of the Invention

This invention relates to a process for drying hydrogen fluoride-carboxylic acid mixtures, i.e., removing water from mixtures of hydrogen fluoride, a carboxylic acid such as acetic acid, and water.

2. Description of Related Art

The following information is disclosed in accordance with the terms of 37 CFR 1.56, 1.97, and 1.98.

Aromatic ketones which can be produced by Friedel-Crafts acylations using hydrogen fluoride as catalyst are possible intermediates for a variety of products having a multiplicity of end uses. Thus, U.S. Pat. No. 4,524,217, issued June 18, 1985 to Davenport et al., discloses a process of using hydroxy aromatic ketones, e.g., 4-hydroxyacetophenone (4-HAP), to make N-acyl-hydroxy aromatic amines, e.g., N-acetyl-para-aminophenol (APAP), better known as acetaminophen, which has wide use as an analgesic. U.S. Pat. No. 4,568,763, issued Feb. 4, 1986 to Davenport et al., discloses the use of hydroxy aromatic ketones such as 4-HAP as an intermediate for the production of N-acyl-acyloxy aromatic amines, e.g., 4-acetoxyacetanilide (4-AAA), which can be used for the preparation of poly(ester-amide)s capable of forming an anisotropic melt phase and suitable for being formed into shaped articles such as moldings, fibers, and films. In addition, 4-AAA may also be hydrolyzed to form APAP. U.S. Pat. No. 4,692,546, issued Sept. 8, 1987 to Davenport, discloses a process wherein hydroxy aromatic ketones, e.g., 4-HAP, are used to produce acyloxy aromatic carboxylic acids, e.g., 4-acetoxybenzoic acid (4-ABA), which is also capable of being used directly to make polymers which can be formed into an anistropic melt suitable for the formation of shaped articles. Moreover, 4-ABA can be hydrolyzed to 4-hydroxybenzoic acid (4-HBA) which can be used as an intermediate for the production of preservatives, dyes, and fungicides. Pending U.S. patent application Ser. Nos. 661,552, filed Oct. 17, 1984 by Gerberich, and 689,533, filed Jan. 7, 1985 by Hilton, disclose processes wherein hydroxy aromatic ketones, e.g., 4-HAP, are used as intermediates for the production of aromatic diols, e.g., hydroquinone, which has utility as a photographic developer, polymerization inhibitor, dye intermediate, and anti-oxidant.

The foregoing U.S. patents and pending applications each shows the production of aromatic ketones by the Friedel-Crafts acylation of aromatic compounds with a carboxylic acid using hydrogen fluoride as catalyst. In addition to these disclosures, pending applications Ser. Nos. 716,016, filed Mar. 26, 1985 by Mott et al., and 106,940, filed Oct. 8, 1987 by Davenport et al., teach processes for the production of 4-HAP by the Friedel-Crafts acetylation of phenol with acetic acid utilizing hydrogen fluoride as catalyst and reaction conditions within certain prescribed ranges.

The following published patents and literature articles as well as pending U.S. patent applications also teach processes utilizing hydrogen fluoride in the production of aromatic ketones by the Friedel-Crafts acylation of aromatic compounds using a carboxylic acid such as acetic as acylating agent:

U.S. Pat. No. 4,593,125, issued June 3, 1986 to Davenport et al., shows the acylation of various substituted naphthalenes using hydrogen fluoride as catalyst to obtain the corresponding substituted naphthones, e.g., 6-hydroxy-2-acetonaphthone (6,2-HAN).

Dann et al. in a dissertation included as part of a series of Reports from the Institute for Applied Chemistry of the University of Erlangen, received for publication on Jan. 7, 1954 and published in Annalen der Chemie 587 Band, pages 1 to 15, disclose the acetylation of guaicol with acetic acid to produce a mixture of 4-hydroxy-3-methoxyacetophenone and 3-hydroxy-4-methoxyacetophenone, and the acetylation of phenol with acetic acid to produce 4-HAP, all in the presence of hydrogen fluoride as catalyst.

Simons et al., Journal of the American Chemical Society, 61, 1795 and 1796 (1939), teach the acylation of aromatic compounds using hydrogen fluoride as a condensing agent and in Table 1 on page 1796 show the acetylation of toluene with acetic acid to product p-methylacetophenone, the reaction of toluene and valeric acid to produce p-tolyl n-butyl ketone, and the reaction of toluene with benzoic acid to produce p-tolyl phenyl ketone, as well as the acetylation of phenol with acetic acid to produce 4-HAP.

Pending application Ser. No. 158,141 filed Mar. 4, 1988 by Elango et al., shows the production of 4'-isobutylacetophenone by the Friedel-Crafts acetylation of isobutylbenzene with an acetylating agent which may be acetic acid, using a catalyst which may be hydrogen fluoride. The 4'-isobutylacetophenone is disclosed as an intermediate in a process for the production of ibuprofen.

Other references of interest are as follows:

Kelley, U.S. Pat. No. 2,388,156, issued Oct. 30, 1945, discloses the removal of water from an azeotropic mixture of hydrogen fluoride and water by contracting the mixture with a liquid hydrocarbon solution containing a relatively water-insoluble organic nitrogen base to form an organic hydrofluoride which is more soluble in the hydrocarbon than in water. The hydrocarbon solution of hydrofluoride is then heated to liberate hydrogen fluoride which is recovered.

Cohen, European Patent Publication No. 71,293, published Feb. 9, 1983, teaches the separation of carboxylic acids from mixtures with non-acids such as water by extraction with a lower lactam such as N-methyl-2-pyrrolidone.

Other references cited by Cohen and showing the use of organic bases to separate carboxylic acids from non-acids such as water, are U.S. Pat. No. 3,878,241 (1,2-dimorpholinoethane); DE-A 2,408,011 (N-methylacetamide); DE-A 2,545,730 (N-formyl morpholine); U.S. Pat. No. 3,478,093 (lactams immiscible with mixture to be separated); and DE-A 2,545,658 (secondary amides).

In general, processes for producing aromatic ketones by acylating an aromatic compound with a carboxylic acid utilizing hydrogen fluoride as a catalyst employ an excess of hydrogen fluoride and carboxylic acid and result in a product mixture comprising hydrogen fluoride, water and carboxylic acid as well as aromatic ketone product, which mixture must be purified both to obtain aromatic ketone of sufficient purity to make it suitable for further use, and to recover the hydrogen fluoride and carboxylic acid for recycling to the process.

One method of purification includes an initial solvent-assisted distillation of the mixture as disclosed, for example, in U.S. Pat. No. 4,663,485, issued May 5, 1987 to Murphy et al., and pending application Ser. No. 013,311 filed Feb. 11, 1987 by Murphy et al. In this method, a composition comprising an aromatic ketone, e.g., 4-hydroxyacetophenone (4-HAP), and an inorganic fluoride consisting essentially of hydrogen fluoride (HF), is distilled in a column or other vessel in the presence of an assisting solvent which is stable in the presence of HF. The vapor overhead comprises a major portion of the HF in the feed to the distillation vessel mixed with some assisting solvent. A liquid residue containing solvent and most of the aromatic ketone in the feed and which may contain heavy ends other than the desired aromatic ketone, is obtained from the base of the column. When the composition being purified is that resulting from the acylation of an aromatic compound with a free carboxylic acid using HF as a catalyst, and thus contains water and carboxylic acid as well as aromatic ketone and HF, then the overhead in the solvent-assisted distillation column will contain water and some carboxylic acid as well as HF and the assisting solvent. After separation of the assisting solvent by decantation or distillation (assuming the assisting solvent is not the carboxylic acid) the composition remaining will comprise HF, carboxylic acid and water, with possibly a small amount of assisting solvent. However, before recycling HF and carboxylic acid to the process (a step necessary for economic reasons), the water must be removed or substantially reduced in content since its presence inhibits the acylation reaction due to equilibrium considerations.

Although the vapor pressures of the pure components may indicate that a water-HF-carboxylic acid mixture should be easily separated, azeotropes and the non-idealities often make the separation difficult. For example, HF forms a high-boiling azeotrope with both water and various carboxylic acids such as acetic. While water and a carboxylic acid such as acetic do not form an azeotrope, their relative volatilities are lower than ideal solution laws predict.

SUMMARY OF THE INVENTION

In accordance with this invention, all or most of the water is removed from a mixture comprising HF, a carboxylic acid and water by extractive distillation in the presence of a Lewis base as solvent, which does not azeotrope with water, forms bonds with the HF and carboxylic acid which can be broken by heat, and has a boiling point at atmospheric pressure of at least 20° C. above that of the carboxylic acid. In carrying out the extractive distillation, most of the HF and carboxylic acid bonded to the Lewis base travel down the column while water and non-acid light compounds, i.e., having boiling points not much above that of water, go overhead. The complexes of the Lewis base with HF and carboxylic acid are then subjected to a solvent regeneration distillation to break the bonds with the Lewis base such that most of the HF and carboxylic acid are taken overhead and recycled to the acylation reaction, while most of the Lewis base solvent forms the residue and is recycled to the extractive distillation column.

If more HF is present in the mixture than is necessary to form azeotropes with the water and carboxylic acid, the excess HF is distilled out in an HF recovery column and returned directly to the reaction before the remaining mixture is subjected to extractive distillation with the Lewis base solvent as described.

DESCRIPTION OF SPECIFIC EMBODIMENTS

The mixtures comprising HF, a carboxylic acid and water contemplated to be treated by the process of this invention to remove all or most of the water are in most cases obtained as a result of the Friedel-Crafts acylation of aromatic compounds with a carboxylic acid, using HF as a catalyst to produce aromatic ketones having the formula:

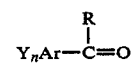

where Ar is the residue of an unsubstituted aromatic hydrocarbon, preferably benzene, naphthalene or biphenyl, wherein hydrogen atoms are substituted with the keto carbon atom and Y's indicated in the formula, n is an integer in the range of zero to about 5, preferably 1 to 3, and the Y's may be any substituent which is stable in the presence of HF and does not cause the ketone to decompose on melting, such as hydroxy, sulfhydryl, halide, e.g., fluoride, chloride, bromide, or iodide and/or organic, e.g., alkyl, alkoxy, acyloxy, or alkylthio, containing from 1 to about 18 carbon atoms, preferably 1 to 4 carbon atoms. In cases where there are at least two Y's bonded to the aromatic nucleus, they may be the same or different.

The R group in the foregoing formula is an alkyl group containing, for example 1 to 10 carbon atoms, preferably 1 to 4 carbon atoms, or aryl, e.g., phenyl or naphthyl. More preferably, R is methyl, ethyl, propyl, or phenyl and most preferably methyl, such that the aromatic ketone being purified is an aromatic methyl ketone.

A group of aromatic ketones of particular interest, the production of which results in mixtures suitable to being purified by the process of this invention, are hydroxy aromatic ketones such that, in the foregoing formula, Y is hydroxy, n is 1, R is methyl, and Ar is 1,4-phenylene, 2,6-naphthlene, 2,1-naphthylene, 5-phenyl-1,2-phenylene, 3-phenyl-1,4-phenylene, or 3-methyl-1,4-phenylene, with the ketocarbon occupying the first stated numbered position of Ar when the positions are not equivalent. Most preferably Ar is 1,4-phenylene or 2,6-naphthalene, and the hydroxy aromatic ketone being purified is 4-HAP or 6,2-HAN.

Another group of aromatic ketones the production of which may result in a mixture suitable for drying by means of the process of this invention are alkylaromatic ketones, e.g., 4-alkylacetophenones such as 4-methylacetophenone and 4-isobutylacetophenone.

Still another group of aromatic ketones whose production may result in a mixture suitable for removal of water by the process of this invention are the benzophenones, wherein Ar in the foregoing formula is a benzene residue and R is phenyl, e.g., 2,3,4-trihydroxybenzophenone.

The compositions containing HF, a carboxylic acid, and water, which are treated to remove water utilizing the process of this invention are obtained, for example, as a stream in the purification of a product mixture from the production of aromatic ketones, e.g., 4-HAP, by the Friedel-Crafts acylation of an aromatic compound, e.g., phenol, with a carboxylic acid, e.g., acetic, using HF as catalyst as taught, for example in the previously cited disclosures. In most cases, such product mixtures contain a molar preponderance of liquid HF in which is dissolved a product of reaction composed primarily of the desired aromatic ketone together with minor amounts of impurities such as isomeric aromatic ketones, e.g., 2-hydroxyacetophenone (2-HAP), when 4-HAP is the desired product, and excess carboxylic acid. Depending on the conditions of the process used to produce it, the amount of aromatic ketone in the composition, excluding the HF, may be, for example in the range of about 25 to 98 weight percent, while the mole ratio of HF to aromatic ketone plus impurities may be, for example, about the same as the mole ratio of HF to initial aromatic reactant, e.g., phenol. As more fully discussed below, this mole ratio may be, for example, about 7 to 80.

The product mixture as described must first be purified to remove aromatic ketone product before a mixture can be obtained which is suitable for the treatment to remove water by the extractive distillation process of this invention. A particularly suitable purification process for this purpose is a solvent-assisted distillation (SAD) of the type previously described, and disclosed in previously cited U.S. Pat. No. 4,663,485 and application Ser. No. 013,311, the entire disclosures of which are incorporated by reference. The assisting solvent utilized in such a process may be any compound which has a boiling point at atmospheric pressure not greater than about 200° C. and is stable with respect to HF. Moreover, the assisting solvent should either be substantially immiscible with HF and the aromatic ketone product considered separately, in the liquid phase, or HF and/or the ketone should be capable of being recovered from the assisting solvent by some method, e.g., distillation or crystallization. The assisting solvent may be, for example, an alkane having, for example, about 4 to 16 carbon atoms, which may be straight chain, branched, or cyclic, and is preferably a straight chain alkane having 5 to 9 carbon atoms, most preferably 6 to 8 carbon atoms; a single ring aromatic compound such as benzene or toluene; an aliphatic carboxylic acid limited in composition to carbon, hydrogen and oxygen and having at least two carbon atoms, e.g., an alkanoic acid having 2 to 12 carbon atoms such as acetic, propionic, n-butyric and valeric acids (which are stable in HF but do not form second liquid phases when in contact with HF); a halogenated aliphatic or cycloaliphatic hydrocarbon, e.g., halogenated alkanes and cycloalkanes, or a halogenated aromatic hydrocarbon such as the fluorinated benzenes, monohalogenated benzenes, and the dichlorobenzenes.

In general, a sufficient amount of assisting solvent is used in the SAD distillation vessel to provide for efficient separation of HF from aromatic ketone with a minimum of ketone degradation. Thus, the ratio of assisting solvent to HF must be high enough to provide the latent heat necessary to volatilize the HF. In many cases, the quality of assisting solvent is such that the assisting solvent/feed ratio (L/F) is at least about 1, preferably about 1 to 15, and most preferably about 2 to 5.

The residue from the SAD column comprises the aromatic ketone product and assisting solvent which is generally subject to further purification to obtain ketone sufficiently pure for subsequent use, and assisting solvent suitable for recycle to the column. The overhead vapors are condensed to form either immiscible HF-rich and solvent rich layers, if the assisting solvent is immiscible with HF, e.g., an alkane, or a homogenous liquid if the assisting solvent is miscible with HF, e.g., an alkanoic acid such as acetic. In the former case, the assisting solvent-rich condensate layer is decanted from the HF layer and returned to the column as reflux. The HF-rich condensate layer contains, in addition to HF, a carboxylic acid such as acetic, and water which is not suitable to be returned to the reactor because of its adverse effect on the equilibrium of the reaction. If the amount of HF present is in excess of that required to form azeotropes with the carboxylic acid and water, then the mixture may be subjected to an "HF recovery" distillation to separate such excess HF free from water, which is recycled to the reaction, and also to separate any assisting solvent present which is recycled to the SAD column. The remaining mixture is then subjected to an extractive distillation in accordance with this invention to reduce its water content and the remaining mixture composed mainly of HF and carboxylic acid is recycled to the reactor.

If the assisting solvent is miscible with HF such that a homogenous condensate is obtained from the solvent-assisted distillation column, the condensate may be subjected to an HF recovery distillation to remove excess HF which is recycled to the reactor and/or all or part of the assisting solvent which is sent back to the SAD column as reflux. If the assisting solvent is a carboxylic acid, e.g., the same acid as utilized in the Friedel-Crafts reaction such as acetic acid, then the condensate will contain an amount of such acid in excess of that necessary to form an azeotrope with the HF, and the condensate may be distilled to remove part but not all of the acid which is recycled to the SAD column. In any case, the mixture remaining after the removal of part of the HF and/or all or part of the assisting solvent is then subjected to the extractive distillation of this invention to remove all or part of the water before the mixture is recycled to the reactor.

As stated, the solvent used in the extractive distillation of this invention is a Lewis base which does not azeotrope with water, forms a bond with each of HF and the carboxylic acid which is broken by heat, and has a boiling point at atmospheric pressure at least 20° C. above that of the carboxylic acid. The solvent may be for example an amide having a total number of carbon atoms between about 4 to 12, e.g., N-alkyl acyclic or cyclic amides wherein the alkyl groups contain 1 to about 4 carbon atoms, such as N-methyl-2-pyrrolidone (NMP), or an amine, having a total number of carbon atoms between about 4 and 42, e.g., trialkyl amines wherein the alkyl groups each contain about 6 to 14 carbon atoms, such as "Adogen 365" produced by Sherex Chemical Company, which is a tri-n-alkylamine wherein the alkyl groups contain about 8 to 10 carbon atoms, or 1,2-dimorpholinoethane (1,2-di-N-morpholylethane). The preferred Lewis base solvent is N-methyl-2-pyrrolidone (NMP).

The carboxylic acid present in the mixture which is extractively distilled in accordance with this invention has the formula RCOOH where R has been defined previously in connection with the definition of the aromatic ketone which is the principal product of the overall process. Thus the carboxylic acid may be an alkanoic acid containing, for example, 2 to 5 carbon atoms, e.g., acetic, propionic, n-butyric or n-valeric, or an aromatic carboxylic acid, e.g., benzoic or 2-naphthoic acid. The most important acid in the application of the inventive process is acetic acid.

In general, the mixture being extractively distilled in accordance with this invention contains most of the water formed as a result of the Friedel-Crafts acylation of aromatic compound with the carboxylic acid to obtain the desired aromatic ketone product, most of the carboxylic acid added to the reactor in excess of that necessary to react with the aromatic compound, and an amount of HF forming an azeotrope with the water and carboxylic acid present. In many cases, the molar ratio of HF to carboxylic acid will be in the range, for example, of about 5 to 80, and the molar ratio of HF to water will be in the range, for example of about 5 to 80.

In carrying out the process, a sufficient amount of extractive Lewis base solvent is used in the extractive distillation vessel to provide for efficient separation of water from HF and carboxylic acid so that the latter compounds can be recycled to the reactor. Thus, the ratio of extractive solvent to HF must be high enough to bond all or most of the HF and carboxylic acid present. In many cases, the molar quantity of extractive solvent is such that the molar extractive solvent/acid ratio (L/F) is at least about 0.5, preferably about 0.5 to 20, and most preferably about 0.5 to 4.

The extractive distillation vessel is generally operated at a base temperature within a range, the minimum of which is that which provides for the vaporization of water in the distillation apparatus, and the maximum of which is the temperature at which the bonds holding the HF and carboxylic acid are broken so that an appreciable amount of HF and carboxylic acid would be vaporized. In general, the minimum operating temperature is several degrees above the boiling point of water at the operating pressure, while the maximum temperature will depend on the Lewis base solvent and carboxylic acid being employed. In most cases, the operating temperature will be in the range of about 120° to 200° C. and the operating pressure in the range of about 0.5 to about 2 atm. When acetic acid is the carboxylic acid and N-methyl-2-pyrrolidone is the Lewis base solvent, the temperature may be in the range of about 160° to 200° C. and the pressure about atmospheric.

The mixture comprising HF, carboxylic acid and Lewis base solvent leaving the extractive distillation vessel as residue is then subjected to a "solvent regeneration" distillation at a temperature and pressure sufficient to break the bonds of the Lewis base solvent with the HF and carboxylic acid, which leave the vessel as vapor overhead and are recycled to the reactor. The residue from this vessel in the Lewis base solvent which is recycled to the extractive distillation. In most cases the operating temperature will be in the range of about 120° to 200° C. and the operating pressure in the range of about 0.1 to about 1.0 atm. When acetic acid is the carboxylic acid and N-methylpyrrolidone is the Lewis base solvent, the temperature may be in the range of about 140° to 180° C. and the pressure in the range of about 0.1 to 0.5 atm.

Any suitable distillation vessels may be used to carry out the extractive distillation and solvent regeneration of this invention. Thus, the vessel may or may not contain interior surfaces serving to implement condensation and re-vaporization of the constituents of the composition being separated, e.g., packing, trays, and the like. For continuous or semi-continuous operation, the use of fractionating columns, e.g., packed columns or columns containing trays are particularly suitable. When operating continuously, the feed composition and Lewis base extractive solvent may be premixed before entering the extractive distillation column. Preferably, however, they are injected into the column at separate points, with the solvent above the feed.

The extractive distillation process of this invention is preferably integrated with a process for the production of aromatic ketone, e.g., 4-HAP, by the Friedel-Crafts acylation of an aromatic compound, e.g., phenol, with a carboxylic acid, e.g., acetic acid, utilizing HF as a catalyst, as described for example in the previously cited U.S. patents and patent applications and literature references, and also with the solvent-assisted distillation (SAD) process as described, for example, in the previously cited U.S. Pat. No. 4,663,485 and pending application Ser. No. 013,311. An integrated process of this type is illustrated in the drawing which is a schematic representation of such a process. As indicated in the drawing, desired amounts of hydrogen fluoride (HF), an aromatic compound such as phenol, and a carboxylic acid such as acetic are passed into reactor 1 through lines 2, 3 and 4 respectively. In the reactor, the aromatic compound and carboxylic acid react in a Friedel-Crafts acylation reaction utilizing HF as a catalyst and solvent to produce an aromatic ketone, e.g., 4-hydroxyacetophenone (4-HAP) and water of reaction. A product mixture comprising aromatic ketone product, water, excess HF and excess carboxylic acid, leaves reactor 1 by line 5 and is passed into solvent assisted distillation (SAD) column 6 where it is distilled in the presence of an assisting solvent, e.g., an alkane such as hexane as disclosed in U.S. Pat. No. 4,663,485 and pending application Ser. No. 013,311. The distillation in SAD column 6 results in a liquid base product comprising predominantly aromatic ketone product and assisting solvent which leaves the column through line 7 and is subsequently further treated to obtain aromatic ketone of requisite purity, and a vapor overhead comprising HF, water, carboxylic acid and assisting solvent, which leaves the column through line 8 and is condensed in decanter 9. If the assisting solvent is water immiscible, e.g., an alkane such as n-hexane, the condensate separates into two layers, an aqueous layer 10 comprising predominantly water, HF, and carboxylic acid, and an organic layer 11 which is predominantly assisting solvent and is decanted and returned to SAD column 6 as reflux through line 12. Alternatively, if the assisting solvent is water miscible, the vapor overhead may be passed to a distillation column (not shown) where the assisting solvent, which may be the same carboxylic acid, e.g. acetic acid, as is used in the reaction, is separated and returned to SAD column 6 as reflux. Either aqueous layer 10 (if the assisting solvent is water-immiscible), or the remainder of the distillation after the assisting solvent is separated and returned to SAD column (if the assisting solvent is water miscible), is composed primarily of HF, water and carboxylic acid. If the latter mixture contains an amount of HF in excess of that required to form azeotropes with the water and carboxylic acid, as is usually the case when a water immiscible assisting solvent is used which can be decanted from condenser 9, then the mixture is passed through line 13 to HF recovery column 14 where the excess HF is obtained as overhead and is recycled to reactor 1 through line 15. The base product of column 14 which is composed predominantly of HF azeotroped with water and carboxylic acid, and a small amount of SAD assisting solvent from SAD column 6, is passed through line 16 into water-stripper extractive distillation column 17 where it is distilled with a Lewis base solvent, e.g., N-methyl-2-pyrrolidone (NMP), entering column 17 through line 28. The Lewis base solvent binds with the HF and carboxylic acid thus liberating the water and any SAD assisting solvent which are removed from he column as vapor overhead. If the SAD assisting solvent is water immiscible, the overhead vapor from column 17 may be passed through line 18 to overhead decanter 19 where, in the absence of any appreciable amount of carboxylic acid, the water and SAD assisting solvent separate into two layers, organic layer 20 which may be recycled through line 21 to SAD column 6, and aqueous layer 22 part of which may be returned to column 17 through line 23 as reflux and part withdrawn through line 24 and disposed of. The base product from column 17, composed primarily of HF, carboxylic acid and Lewis base, is passed through line 25 to Lewis base solvent regeneration column 26 where it is distilled at the temperatures high enough to break the bonds between the Lewis base solvent and the HF and carboxylic acid. The latter two compounds are thus withdrawn from columns 26 as vapor overhead and recycled to reactor 1 substantially free of water through line 27, while the Lewis base solvent, which may contain recycle amounts of acids, is withdrawn as liquid base product and recycled through line 28 to column 17.

When 4-HAP is being purified, the phenol, acetic acid, and HF catalyst, may be charged to corrosion-resistant reactor 1 and the mixture maintained at a temperature, for example, of about 20° to about 100° C. for a period, for example, of about ½ to about 4 hours, at a pressure, for example, of about 50 to about 500 psig. The HF may be charged as a liquid or a gas using technologies of handling well-known to those skilled in the art. In carrying out the reaction, an inert gas such as nitrogen may be used to keep the reaction space under the desired pressure and sufficient HF in contact with the reacting liquid. An excess of HF is generally used, for example, about 7 to about 80 moles per mole of phenyl acetate or phenol initially present in the reaction zone.

SAD distillation column 6 is generally operated at a base temperature within a range, the minimum of which is that which prevents solid ketone formation in the distillation apparatus, and the maximum of which is the temperature at which the aromatic ketone significantly degrades. When the aromatic ketone is not appreciably soluble in the assisting solvent as is the case with 4-HAP as the aromatic ketone and an alkane as assisting solvent, the minimum operating temperature is about the melting point of the ketone. When 4-HAP is being purified, the operating temperature is suitably in the range of about 110° to 140°, preferably about 110° to 130° C. In most cases, the pressure is in the range of about 0.1 to 10 atm., preferably about 1 to 50 psig. In general, it is desirable for the pressure to be high enough to allow condensation of the HF in the overhead without refrigeration.

As previously mentioned, because of the large excess of HF used in reactor 1, the vapor overhead leaving SAD column 6 generally contains an amount of HF substantially in excess of that necessary to form azeotropes with the water and carboxylic acid present (assuming the carboxylic acid is not being used as the assisting solvent). Such excess HF is advantageously removed from the mixture before the mixture is subjected to the extractive distillation of this invention, e.g., in column 17 of the drawing. This may be done in a separate distillation, e.g., as illustrated by HF recovery column 14 of the drawing. If 4-HAP is the aromatic ketone being produced and purified and an alkane such as n-hexane is the assisting solvent in SAD column 6 such that the mixture entering column 14 is composed primarily of excess HF, acetic acid, water and a small amount of alkane, the HF recovery column 14 will generally be operated, for example, at a base temperature of about 120° to 170° C. and a pressure of about 1 to 4 atm., with the temperature and pressure being correlated so that a vapor composed almost entirely of HF is returned to reactor 1 through line 15.

The mixture leaving HF recovery column 14 as residue through line 16 is the mixture which is treated to remove water of reaction, e.g., in water-stripper extractive distillation column 17 and solvent regeneration column 26, by the extractive distillation process of this invention, the conditions for which have been described previously.

The following examples further illustrate the extractive distillation process of the invention. Examples 1 and 2 are batch distillations of mixtures of HF, acetic acid and water to which N-methyl-2-pyrrolidone (NMP) is added as extractive solvent. The distillations are carried out at different pressures which simulate the operation of a fractionating column intended to strip water from the mixture and also, in Example 2, to separate NMP from the HF and acetic acid.

The distillations were carried out in a Teflon batch still. Indirect heat to the reboiler was provided by an oil bath. The temperature in the reboiler was measured by a thermocouple inserted into the pot in a Teflon sheath. A tube extended into the reboiler for sampling the liquid. The column pressure was measured by a Monel vacuum pressure gauge. The column was packed with Teflon shavings. The overhead sample collection system was modified by introducing translucent Teflon; this allowed visual inspection of the overhead flow rates, and collection of 30 ml overhead fractions in Teflon sample bottles with valved lids for sample analysis. Once 12 overhead fractions were collected, they were directly analyzed for water using Karl-Fischer analysis. The samples were then neutralized with 45 wt % aqueous potassium hydroxide, and the mixture analyzed for fluoride, acetate, and NMP.

EXAMPLE 1

This distillation was carried out at 215 mm HgA on a mixture consisting of 25 g of HF, 41 g of water and 75 g of acetic acid (HOAc) to which were added 347 g of N-methyl-2-pyrrolidone (NMP) as extractive solvent. The results showing the compositions of the 12 overhead fractions collected and the temperatures in the base at each collection are shown in Table I:

TABLE I

| Sample | Overhead Composition | | | | Temp. in Base °C. |
|---|---|---|---|---|---|
| | Water wt % | HF wt % | HOAc wt % | NMP wt % | |
| 1 | 81.5 | 0.06 | 13.0 | 5.4 | 144.3 |
| 2 | 62.0 | 0.65 | 28.4 | 8.9 | 159.8 |
| 3 | 20.3 | 2.94 | 49.4 | 27.4 | 163.7 |
| 4 | 12.0 | 3.25 | 48.1 | 36.6 | 163.9 |
| 5 | 4.2 | 3.91 | 41.1 | 50.8 | 164.6 |
| 6 | 2.4 | 4.43 | 37.0 | 56.2 | 164.7 |
| 7 | 1.3 | 4.85 | 32.1 | 61.7 | 165.8 |
| 8 | 0.7 | 5.09 | 26.5 | 67.8 | 166.6 |
| 9 | 0.5 | 2.53 | 21.9 | 72.1 | 167.4 |
| 10 | 0.2 | 5.53 | 18.7 | 75.6 | 167.2 |
| 11 | 0.3 | 5.87 | 13.9 | 80.0 | 167.4 |

TABLE I-continued

| Sample | Overhead Composition | | | | Temp. in Base °C. |
|---|---|---|---|---|---|
| | Water wt % | HF wt % | HOAc wt % | NMP wt % | |
| 12 | 0.1 | 6.20 | 9.7 | 84.0 | 167.4 |

The results of this example, particularly as shown in the composition of sample 1 of Table I, indicate that the extractive distillation of this invention can be effectively used to remove water from an HF-water-acetic acid mixture without loss of significant amounts of HF and acetic acid.

EXAMPLE 2

This distillation was similar to that of Example I except that the pressure varied between 355 and 469 mm HgA and the mixture to be dried consisted of 50 g HF, 50 g water and 75 g acetic acid, to which were added 350 g NMP as extractive solvent. The results are shown in Table II, which includes both the temperatures and pressures in the system at the withdrawal of each sample:

TABLE II

| Sample | Overhead Composition | | | | Temp. in Base °C. | Press mm HgA |
|---|---|---|---|---|---|---|
| | Water wt % | HF wt % | HOAc wt % | NMP wt % | | |
| 1 | 64.29 | 2.34 | 33.25 | 0.21 | 134.2 | 469 |
| 2 | 68.50 | 2.69 | 28.65 | 0.16 | 188.9 | 481 |
| 3 | 47.90 | 7.44 | 43.57 | 1.09 | 186.5 | 431 |
| 4 | 29.30 | 11.50 | 54.26 | 5.94 | 186.0 | 380 |
| 5 | 15.70 | 13.17 | 46.85 | 24.28 | 184.4 | 380 |
| 6 | 7.30 | 12.82 | 33.84 | 46.04 | 184.8 | 375 |
| 7 | 2.58 | 11.36 | 19.28 | 66.78 | 183.3 | 367 |
| 8 | 1.21 | 9.78 | 12.29 | 76.72 | 183.5 | 367 |
| 9 | 0.96 | 10.77 | 10.26 | 78.01 | 183.2 | 355 |
| 10 | 1.03 | 9.30 | 6.67 | 83.00 | 183.6 | 355 |
| 11 | 1.11 | 8.88 | 4.50 | 85.51 | 183.9 | 355 |
| 12 | 0.61 | 8.32 | 3.37 | 87.70 | 183.8 | 355 |

The results of this example, particularly the "peak" of acetic acid in the overhead of sample 4, and the "peak" of HF in the overhead of sample 5, in both of which the NMP is present in minor amount which is considerably less than the NMP content of later samples, indicate that acetic acid and HF can be separated from NMP in a fractional distillation process with the NMP re-used in the process. Thus, the overall effect of the extractive distillation of this invention is the effective removal of water from mixtures of HF, carboxylic acid and water.

EXAMPLE 3

This example illustrates an integrated process of producing 4-hydroxyacetophone (4-HAP) by the Friedel-Crafts acetylation of phenol with acetic acid using HF as catalyst and solvent, purifying it using an SAD column with n-hexane as assisting solvent, and removing water of reaction from the recycle stream using the extractive distillation of this invention with NMP as Lewis base solvent, all in accordance with the scheme shown in the drawing.

Into Friedel-Crafts reactor 1 are fed 1 kg mol/h of phenol through line 3, 1.51 kg mol/h of acetic acid (1.25 kg mol/h as fresh feed through line 4 and 0.26 kg mol/h as recycle from solvent regeneration column 26 through line 27), and 30 kg mol/h of HF (about 29.45 kg mol/hr as recycle from the overhead HF recovery column 14 through line 15 which together with a small amount of make-up HF as necessary is fed through line 2, and about 0.55 kg mol/h as recycle from solvent regeneration column 26 through line 27). Reaction takes place in reactor 1 at about 80° C. and 60 psia with a residence time of about 1 hour. An overhead product stream from reactor 1 containing about 0.90 kg mol/h of 4-hydroxyacetophenone (4-HAP), 30 kg mol/h of HF, 0.26 kg mol/h of excess acetic acid, 0.99 kg mol/h of water, 0.01 kg mol/h of phenol and as by-products 0.08 kg mol/hr of 2-hydroxyacetophenone (2-HAP) and 0.01 kg mol/h of heavy ends, leaves reactor 1 by line 5 and enters solvent assisted distillation (SAD) column 6 into which is also fed from decanter 9 through line 12 0.91 kg mol/h of n-hexane as assisting solvent. The SAD column 6 in which HF and acetic acid are distilled from the 4-HAP product stream, operates under base conditions of 125° C. and 45 psia and contains about 12 stages. The base product containing the 4-HAP product, by-products, and small amount of unreacted phenol fed to column 6 through line 5, and also about 0.01 kg mol/hr of n-hexane, is removed from column 6 through line 7 for further processing. Overhead product from column 6 containing substantially all the HF, acetic acid and water previously fed to the column through line 5, and also 0.93 kg mol/h of n-hexane, is fed through line 8 to decanter 9 where it is condensed at 32° C. and 39 psia, and allowed to phase. An n-hexane-rich phase 11 is returned as reflux to column 6 through line 12 and an HF-rich phase 10 containing HF, some n-hexane, water of reaction and excess acetic acid, is sent through line 13 to HF recovery column 14 which operates at 160° C., 46 psia, and a reflux ratio of 0.1, and contains 20 distillation stages for the separation of HF in excess of that forming a high boiling HF/water azeotrope (about 35%) from the other components of the entering stream. The overhead stream from column 14 comprising about 29.45 kg mol/hr of HF is recycled to reactor 1 through line 15, and the base product containing 0.55 kg mol/h of HF azeotroped with 0.99 kg mol/h of water, 0.99 kg mol/h of acetic acid, and 0.03 kg mol/h of n-hexane, is fed through line 16 to water-stripper extractive distillation column 17 which operates under base conditions of 149° C. and 22 psia, contains 12 stages, and in which water and excess n-hexane are separated from HF and acetic acid by extractive distillation using N-methyl pyrrolidone (NMP) as the extractive solvent. The NMP in an amount of 1.75 kg mol/h is fed with steady state recycle amounts of 0.65 kg mol/h of HF and 0.03 kg mol/h of acetic acid through line 28 to column 17 as recycle of the base product from solvent regeneration column 26. Line 28 enters column 17 above line 16 in order to facilitate the complexing of HF and acetic acid. An overhead vapor stream containing 1.09 kg mol/h of water and 0.03 kg mol/h of n-hexane is fed through line 18 to decanter 19 where it is condensed and phases into n-hexane-rich phase 20 in an amount of 0.03 kg mol/h of n-hexane which is withdrawn through line 21 and recycled to SAD column 6, and water-rich phase 22, part of which in an amount of 0.10 kg mol/h of water is recycled to column 17 as reflux through line 23 to prevent NMP or acid from going overhead, and part of which in an amount of 0.99 kg mol/h is withdrawn through line 24 and sent to waste treatment. The base product from column 17 comprising 1.20 kg mol/hr of HF, 0.29 kg mol/hr of acetic acid and 1.75 kgmol/hr of NMP is sent through line 25 to solvent regeneration column 26 which operates with about 7 stages at base conditions of 243° C. and 3 psia, and a reflux ratio of 0.1. An overhead stream comprising 0.55 kg mol/h of HF and 0.26 kg mol/h of acetic acid is recycled to reactor 1 through line 27 and a base product comprising 0.65 kg mol/h of HF, 0.03 kg mol/h of acetic acid, and 1.75 kg mol/h of NMP is recycled through line 28 to column 17 as previously described.

We claim:

1. A process of removing water from a mixture of hydrogen fluoride (HF), a carboxylic acid, and water by extractive distillation in the presence of a Lewis base as solvent, which does not azeotrope with water, forms bonds with the HF and carboxylic acid which can be broken by heat and has a boiling point at atmospheric pressure at least about 20° C. above that of the carboxylic acid, and taking off an overhead vapor comprising a major proportion of the water in said mixture.

2. The process of claim 1 wherein said Lewis base solvent is an amide having a total number of carbon atoms between about 4 and 12, or an amine having a total number of carbon atoms between about 4 and 42.

3. The process of claim 2 wherein said Lewis base is an N-alkyl acyclic or cyclic amide wherein the alkyl groups each contains 1 to 4 carbon atoms or a trialkyl amine wherein the alkyl groups each contains about 6 to 14 carbon atoms.

4. The process of claim 3 wherein said Lewis base is N-methyl-2-pyrrolidone.

5. The process of claim 1 wherein said carboxylic acid is an alkanoic acid containing 2 to 5 carbon atoms, benzoic acid or 2-naphthoic acid.

6. The process of claim 5 wherein said carboxylic acid is acetic acid.

7. The process of claim 1 wherein the residue of said extractive distillation is subjected to a solvent regeneration distillation wherein most of the HF and carboxylic acid in the mixture is taken off as vapor overhead with most of the Lewis base solvent remaining behind as liquid residue 8. A process comprising subjecting an aromatic compound to a Friedel-Crafts acylation with a carboxylic acid in the presence of hydrogen fluoride as catalyst to obtain a product mixture containing an aromatic ketone, hydrogen fluoride, said carboxylic acid, and water of reaction, subjecting said product mixture to a solvent assisted distillation in the presence of an assisting solvent which has an atmospheric boiling point up to about 200° C. and is stable with respect to HF, to obtain an overhead vapor containing said assisting solvent and most of the HF, carboxylic acid, and water of reaction in the product mixture, and a liquid residue containing most of the aromatic ketone in the product mixture, separating assisting solvent from the overhead of said solvent assisted distillation and recycling it to said solvent assisted distillation, subjecting the remainder of the overhead from the solvent assisted distillation comprising hydrogen fluoride, carboxylic acid and water to an HF recovery distillation to separate excess HF as overhead which does not azeotrope with the water and carboxylic acid present, recycling said excess HF to said Friedel-Crafts acylation, subjecting the residue of said HF recovery distillation comprising a mixture of hydrogen fluoride (HF), carboxylic acid, and water to an extractive distillation in the presence of a Lewis base as solvent, which does not azeotrope with water, forms bonds with the HF and carboxylic acid which can be broken by heat and has a boiling point at atmospheric pressure at least about 20° C. above that of the carboxylic acid, taking off an overhead vapor from said extractive distillation comprising a major proportion of the water in said product mixture, subjecting the residue of said extractive distillation to a solvent regeneration distillation, recycling the overhead of said solvent regeneration comprising HF and carboxylic acid to said Friedel-Crafts acylation, and recycling the residue of said solvent regeneration distillation comprising said Lewis base solvent to said extractive distillation.

9. The process of claim 8 wherein said Lewis base solvent is an amide having a total number of carbon atoms between about 4 and 12, or an amine having a total number of carbon atoms between about 4 and 42.

10. The process of claim 9 wherein said Lewis base is an N-alkyl acyclic or cyclic amide wherein the alkyl groups each contains 1 to 4 carbon atoms or a trialkyl amine wherein the alkyl groups each contains about 6 to 14 carbon atoms.

11. The process of claim 10 wherein said Lewis base is N-methyl-2-pyrrolidone.

12. The process of claim 8 wherein said carboxylic acid is an alkanoic acid containing 2 to 5 carbon atoms, benzoic acid or 2-naphthoic acid.

13. The process of claim 12 wherein said carboxylic acid is acetic acid.

14. The process of claim 13 wherein said aromatic compound is phenol and said aromatic ketone is 4-hydroxyacetophenone.

15. The process of claim 8 wherein said assisting solvent is an alkane containing 4 to 16 carbon atoms.

16. The process of claim 15 wherein said alkane solvent is n-hexane.

17. The process of claim 15 wherein said alkane is n-octane.

* * * * *